United States Patent [19]

Kasahara et al.

[11] Patent Number: 5,002,385
[45] Date of Patent: Mar. 26, 1991

[54] TARGET DEVICE USED IN EYE MOVEMENT TESTS

[75] Inventors: Tatsuya Kasahara, Amagasaki; Kuniomi Abe, Kobe; Yoshibumi Udagawa, Nishinomiya, all of Japan

[73] Assignee: Konan Camera Research Institute Inc., Hyogo, Japan

[21] Appl. No.: 472,334

[22] Filed: Jan. 30, 1990

[30] Foreign Application Priority Data

Mar. 14, 1989 [JP] Japan .................................. 1-63250

[51] Int. Cl.$^5$ .............................................. A61B 3/14
[52] U.S. Cl. .................................. 351/210; 351/209; 351/239; 351/211
[58] Field of Search ............... 351/203, 209, 210, 211, 351/224, 239, 243; 128/733, 742

[56] References Cited

U.S. PATENT DOCUMENTS 3,469,903  9/1969  Grichnik et al. .................. 351/209

Primary Examiner—Paul M. Dzierzynski
Attorney, Agent, or Firm—Koda and Androlia

[57] ABSTRACT

A target device used in an eye movement testing device made up of a light group and a refractor. The light group includes a plurality of light sources lined-up side by side behind an window which opens in the front wall of the casing of the testing device, and the refractor is installed to cover the window from the outside of the casing and face the eye to be examined. When the light sources are successively lit on and off, moving virtual images of the light sources are created so that the images which are expanded (to be longer or higher than the light sources) can be seen through the refractor. Thus, the eye movement (nystagmus) induced when the eye follows these types of moving images, is observed.

6 Claims, 2 Drawing Sheets

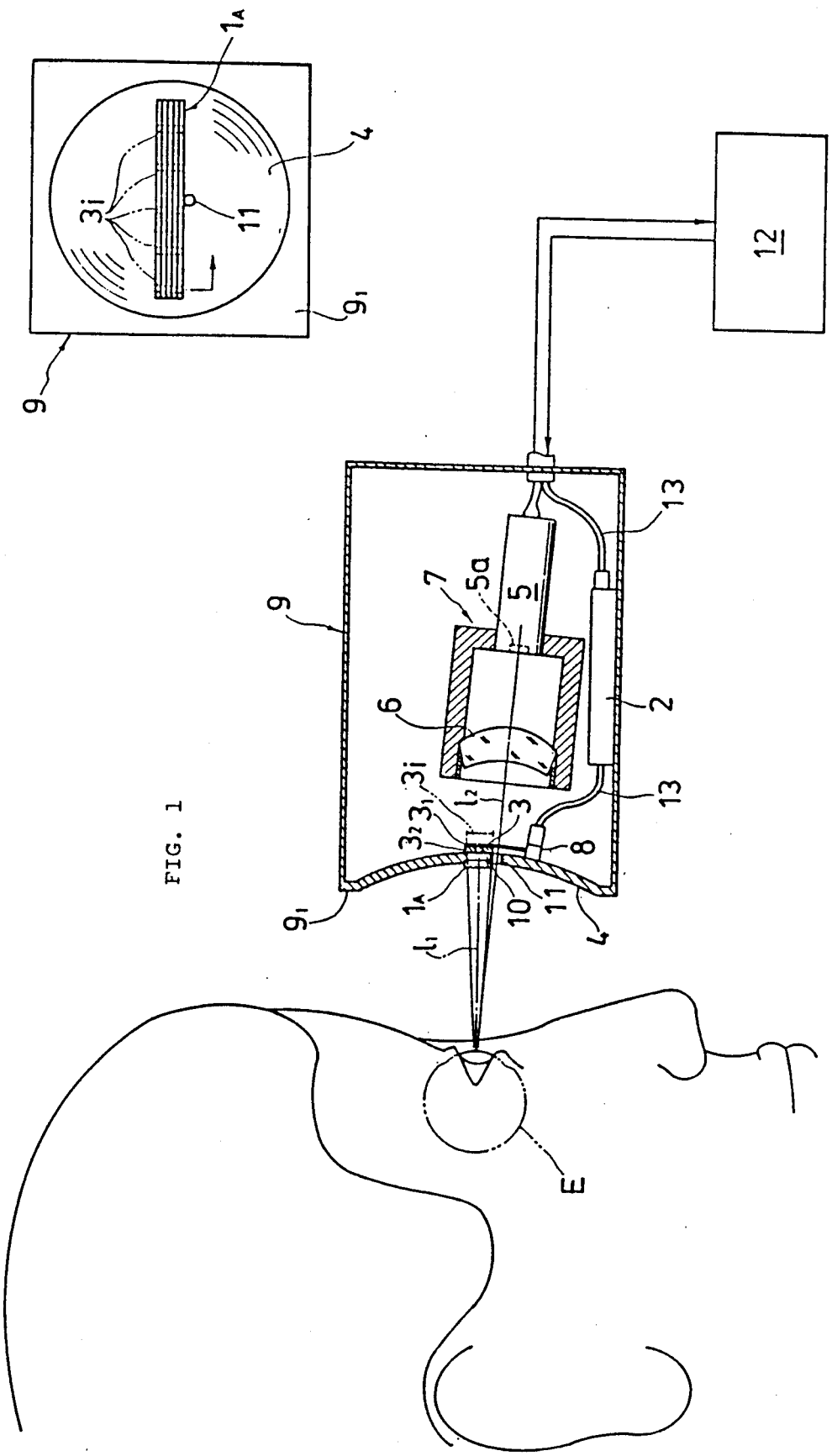

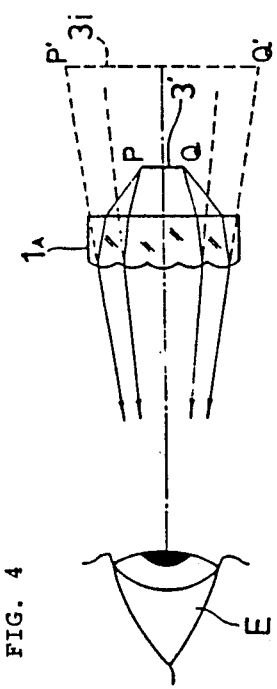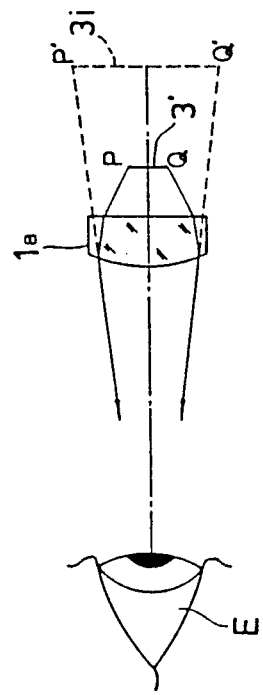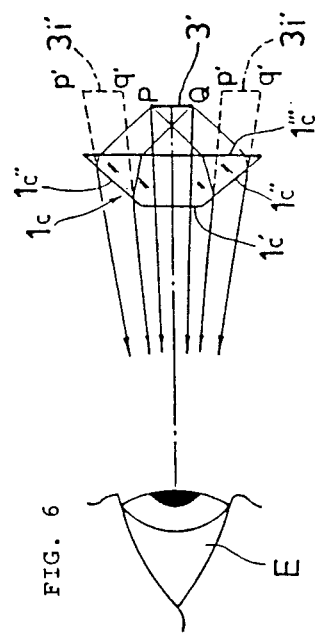
FIG. 4  FIG. 5  FIG. 6
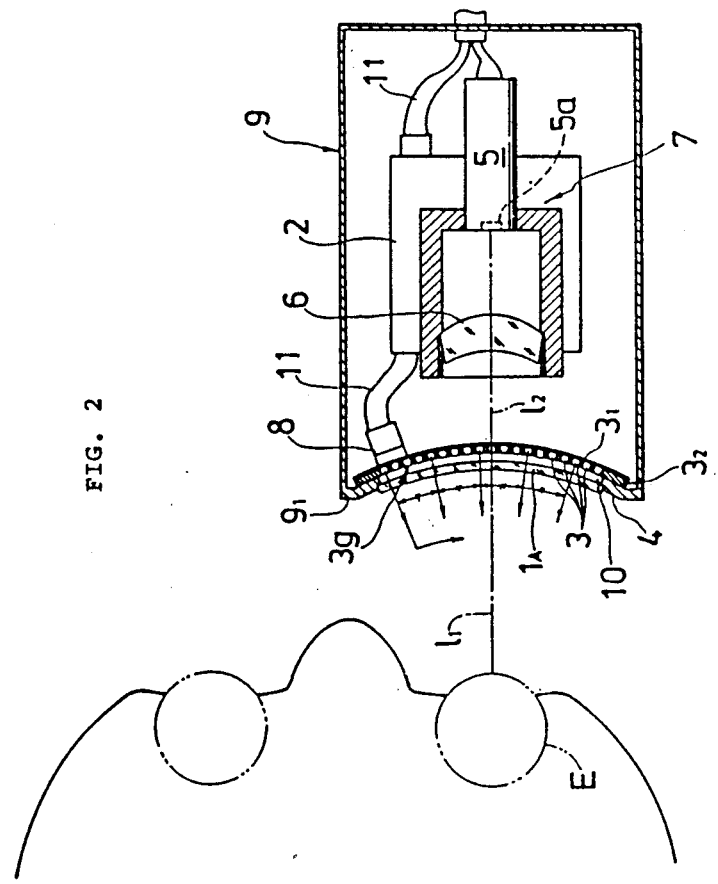
FIG. 2

TARGET DEVICE USED IN EYE MOVEMENT TESTS

BACKGROUND OF THE INVENTION

1. Field of the Invention

The present invention relates to a target device used for examining eye movement and more particularly to a target device for executing an ocular motion nystagmus (eye movement) test in which nystagmus is induced by a stripe pattern target.

2. Prior Art

One of the diagnostic methods used in the clinical examination of a patient's labyrinth, nerves balance or functional disorders of the central nervous system is measurement of eye movement.

Since eye movement tests can reveal symptoms of these problems, various eye movement testing devices are currently used. In these devices, eye movement is tested based upon a condition called "nystagmus" which is obtained when the examinee sees a stationary or movable target.

Of the various types of eye tests, the optical kinetic nystagmus ("OKN") test examines eye movement that is induced to prevent image lag caused by a lag signal generated by an image from the surrounding area formed on the retina when the examinee or the surrounding area around the examinee rotates. The OKN is induced at its maximum when the entire area surrounding the examinee rotates.

Whereas a "follow-the-target" type test tends to induce intentional eye movement with little reactionary eye movement, the OKN test allows for both intentional and reactionary eye movement and thus reveals symptoms of cerebral disease (of a one-sided and extensive disorder or of an acute nature) by measuring the difference between the OKN values of each eye.

The simplified qualitative "follow-the-target" test currently used is a so-called "Tape OKN" test. This test utilizes a tape which is about one meter long with a black-and-white stripe pattern. The tape is moved horizontally or vertically manually in front of the examinee's eyes and OKN induction is thus observed.

Another type of quantitative method used in general practice is one where an examinee enters a rotary drum which has stripe patterns on the inner surface. The drum is rotated electrically, and signals are taken from ENG (electrodes) attached to the top, bottom, left and right sides of the eyes so that the signals are collected, recorded and analyzed.

The above two methods have problems, however. In the Tape OKN test, the tape must be moved manually, and the test result is qualitative, not quantitative. In the second test method which uses the rotary drum, the equipment required is quite large in size, and thus, a large amount of space and manpower are necessary to operate it. Accordingly, this testing method is cumbersome and difficult to implement.

SUMMARY OF THE INVENTION

The present invention was conceived in view of the above problems found in the prior art.

A primary object of the present invention is to provide an ocular target device for eye movement tests in which OKN is induced by moving striped targets in front of the examinee's eyes using a device which is smaller than prior art devices.

Another object of the present invention is to provide an ocular target device wherein measurement of the eye movement is simplified by combining the target device with ENG or replacing the target device with the target device used in the eye movement examination device disclosed in Japanese patent application No. 63-145425 or the eye movement photographing device disclosed in Japanese patent application No. 63-303332, both filed by the applicant of present application.

In order to accomplish the objects of the present invention, a group of light sources and an optical component (refractor) provided on a prescribed curved plane which includes the examinee's ocular axis (visual axes which slightly deviate from the ocular axis) are utilized.

The light source group includes a plurality of visible light sources lined-up so that their respective axis centers are positioned mutually close to each other and the light advances towards the eyes. The lighting (ON or OFF) of the light sources is controlled via a light controller so that the illuminated part of the lined-up light sources successively shift at a prescribed intervals. A refractor having a prescribed width is installed to overlay the lined-up light sources in front of the eyes so that the distance between both ends of virtual images of the light sources are enlarged only in a direction perpendicular to the lined-up light sources (specifically to the length-wise direction of the lined-up light sources).

The refractor positioned in front of the light sources (or between the eyes and the light sources) is lenticular (or wave-shaped) in cross section. Also, the refractor may be arc-shaped (or convex) or trapezoidal in cross section to create virtual images.

In the target device of the present invention, light successively emitted from the visible light sources, which make a target group (the respective axial centers of the target sources are positioned mutually close to each other on a predetermined horizontal or vertical plane), enters the pupil of the eye after being refracted by the refractor. As a result, the examinee can see, through the refractor, virtual images (of the visible light sources) which are expanded only in the direction perpendicular to the length-wise direction of the lined-up light sources (in other words, only in the vertical direction when the light are positioned horizontally).

Thus, when the lined-up visible light sources are illuminated in regular succession and the illuminated position is shifted at predetermined intervals, the examinee can follow the repeated movement of the striped enlarged virtual image, causing OKN.

When the refractor is lenticular or arc-shaped in cross section, the examinee sees the movement of stripe pattern images enlarged in one direction only, and when the refractor is of trapezoidal cross section, the examinee can see three images which are brighter than the previous two images.

BRIEF DESCRIPTION OF THE DRAWING

FIG. 1 is a vertical sectional view of the main part of an eye movement photographing device equipped with the target device of the present invention, in which a lenticular plate is used as an optical component to refract light;

FIG. 2 is a transverse plan view of the main part of the eye movement photographing device of FIG. 1;

FIG. 3 is a front view of the eye movement photographing device of FIG. 1;

FIG. 4 illustrates the light path when the enlarged light source image is seen through the lenticular plate;

FIG. 5 illustrates the light path when the enlarged light source image is seen through the arc-shaped refractor; and FIG. 6 illustrates the light path when the three light source images are seen through the trapezoidal refractor.

DETAILED DESCRIPTION OF THE INVENTION

FIGS. 1 through 3 illustrate the entire target device of the present invention used in an eye movement photographing device for examining eye movement.

The target device in this embodiment is for testing movement of a single eye by successively producing vertical stripes of light and moving them horizontally (i.e., in the same direction as the two eyes). Their vertical stripes are produced by successively lighting the light sources so that the eyes follow the lit light sources. Such a target device is placed in front of the eyes.

More specifically, the embodiment is shown for examining the right eye E. The target device is mounted on the front wall $9_1$ of a casing 9 of the eye movement photographing device which includes target light sources 3, a refractor 1, a television camera 7 and other components.

The miniature television camera 7 is installed in the casing 9 so that it photographs eye movement. A reflector 4 is attached on the outside surface of the front wall $9_1$ of the casing 9. The front wall $9_1$ is in a spherical (or concave) shape around the center of rotational movement of the eye, and the reflector 4 is provided on the front wall $9_1$. The reflector 4 is, for example, painted or coated on the outer surface of the front wall $9_1$.

An oblong window 10 of a prescribed height is provided in the reflector 4 (and the front wall). The window 10 is formed over the plane which includes the ocular axis $1_1$ and another ocular axis so that the examinee can see the target moving (or the target which "looks" as if moving) horizontally.

The window 10 is provided so that targets are viewed therethrough, and behind this window 10, a plurality of (19 in this embodiment) LEDs 3, i.e. the visible light sources, are secured on a flexible base $3_1$ so that they are lined-up side by side. The respective axial lines of the LEDs or the visible light sources 3 are close to each other and directed towards the eye. A light source group 3g is thus formed by the plurality of visible light sources 3 provided on the flexible base $3_1$ and mounted by bonding or other supporting means $3_2$ on the inner side of the front wall $9_1$ of the casing 9.

The power for lighting the LEDs 3 that are fitted on the flexible base $3_1$ is supplied through a connector 8 mounted behind the reflector 4. The LEDs 3 are turned on and off by the connector 8 which is connected to an analyzer 12 through a target controller 2 and flexible cables 13. In the embodiment, the controller 2 and cables 13 are installed in the casing 9 and the analyzer 12 is outside thereof.

A lenticular plate 1A, which is an optical component and works as a refractor, is installed on the front surface of the reflector 4. The lenticular plate 1A (through which the lights from the light sources pass through) has a curved front surface which is lenticular in cross section consisting of mutually proximate multiple arcs. In other words, the lenticular plate 1A has somewhat wave shaped front surface. The back surface of the lenticular plate 1A is flat in the vertical direction.

The lenticular plate 1A as a whole is arc shaped when viewed from the top and centered around the eye-rotational movement. In other words, the lenticular plate 1A has the same curvature as the reflector 4 and the light source group 3.

The height of the lenticular plate 1A is slightly higher than the window 11 so that the lenticular plate 1A covers the window 11 completely and the axis of each LED 3 of the light source group 3g crosses perpendicular to the vertically flat back surface of the lenticular plate 1A. A prescribed distance remains between the back surface of the lenticular plate 1A and each of the LEDs 3.

When the lined-up LEDs 3 are lighted and illuminated successively and alternately, the light from the light-emitting part 3' of the light source having the height P-Q, as shown in FIG. 4, passes through the back of the lenticular plate 1A. The light is then refracted by a plurality of arcs on the front surface of the lenticular plate 1A and enters the pupil. Thus, the examinee can see a vertically extending virtual image $3i$ of the light-emitting part 3' of the light source 3. Such image is enlarged only in the vertical direction so that the height P-Q of the light-emitting part 3' is vertically enlarged to be a virtual image having the height P'-Q'.

Accordingly, by controlling the LEDs 3 so that each LED is illuminated successively at prescribed intervals (in the embodiment, every fourth LED as seen in FIG. 2), the examinee sees moving striped light images ($3i, 3i, 3i, ...$) of the same width as the light-emitting part of the LED 3 and about the same height as (or slightly higher than) the lenticular plate 1A, as they move successively at prescribed intervals (FIG. 3).

With the lenticular plate 1A described above, the light source image seen by the examinee is changed at its minimum even if the ocular axis $1_1$ of the examinee which should be positioned in the center of the lenticular plate 1A is slightly divergent in the vertical direction. Thus, the light source image will definitely reach the eye even if disturbed by small movements in of the eye's position.

A circular window 11 is opened below the center of the intersecting point of the circular (or concave) reflector 4 and the ocular axis $1_1$, so that the circular window 11 almost contacts the lower end of the lenticular plate 1A (FIG. 3).

As seen in FIGS. 1 and 2, the television camera 7 is installed on the light path of the eyeball image behind the window 11 (only the light path passing through the center is illustrated for the sake of explanation). The television camera 7 includes a subminiature image orthicon 5 with a front-aperture-type shooting lens 6 and a light-receiving element 5a such as a CCD at the front end. The front-aperture-type shooting lens 6 is placed so that the front aperture is positioned at the circular window 11 which is on a light path for taking a picture of the eye's movement.

The optical path of the eye image entering the television camera 7 is arranged so that it will form a narrow bundle of light at the point passing through the reflector 4 in order not to interfere with either the reflector 4 or the lenticular plate 1A. As a result, the optical axis $1_2$ of the television camera 7 is positioned as close to the ocular axis $1_1$ as possible to make it quasi-coaxial with the ocular axis $1_1$ and the image formed on the light-receiving element 5a is distorted as little as possible and testing precision is enhanced.

In the above embodiment, the lenticular plate 1A with a multiple number of vertically arranged small arcs on its front surface (forming a wave shaped surface) used as a refractor to enlarge the image of the light sources 3g of the LEDs 3 in the vertical direction.

As an alternative to using this refractor as an optical component (lenticular plate 1A), a horizontally long convex lens 1B as shown in FIG. 5 can be used. The convex lens 1B has a single arc shape on the front surface and a vertically flat back surface. The lens 1B has a prescribed height and width and in a arc-shape (when viewed from the top) which is centered around the eye-rotational center.

The lens 1B thus designed is (like the lenticular plate 1A) mounted in front of the reflector 4 so that the axis of each the LEDs 3 of the light source group 3g and the back surface of the convex lens 1B cross perpendicular to each other. A space is left between the lens 1B and the front edge of each LED 3.

In other words, the lenticular plate 1A in FIG. 1 can be replaced with the convex lens 1B of FIG. 5, and when the arcuate convex lens 1B is used as an optical component in front of the light source group 3g, as illustrated in FIG. 5, the light from the light-emitting part 3' having the height P-Q passes through the back surface of the lens 1B and is refracted at the convex front surface and enters the pupil, making the examinee see a vertically enlarged virtual image 3i of the light-emitting part 3g (of the height P-Q) extended to the height P'-Q'.

In this case also, the on and off function of the LEDs 3 are controlled so that they look as if they are successively moving or shifting at prescribed intervals (FIG. 2), just as in the case of the lenticular plate 1A. Thus, the examinee sees the moving target, i.e., striped lights of the same width as the LED 3 and approximately the same height as (or slightly higher than) the cylindrical lens (slightly higher) move successively at certain intervals. When the convex lens 1B is used, there are some defects in that the light path to the pupil is interrupted when the eye is not positioned properly; and as a result, the ocular axis $l_1$ deviates vertically a small amount from the plane on which the axes of the LEDs 3 are located. However, the structure can be simplified in this case.

It is also possible to use an equilateral trapezoid prism 1C as shown in FIG. 6 as a refractor (as an alternative optical component) in place of the lenticular plate 1A and the convex lens 1B. The prism 1C has a top side 1c', bottom side 1c''' and a pair of slanted sides 1c''. The prism 1C is positioned so that the top side 1c' crosses perpendicular to an imaginary plane on which the axes of the LEDs 3 are located. The prism 1C is arcuate as a whole in shape when viewed from the top and is centered around the rotational center of the eye at a prescribed height and length.

As with the previously described optical components, the trapezoid prism 1C is mounted on the front part of the target window 10 of the reflector 4 so that the top side 1c' faces the eye. Though not illustrated in the Figure, the prism 1C is installed in the same manner as the lenticular plate 1A in FIG. 1.

When the trapezoid prism 1C is used as an optical component, the light from the light-emitting part 3' of the height P-Q enters the prism 1C through the bottom side 1c''', passes through the prism and goes out from top side 1c' of the prism 1C to enter the pupil, while the light also is refracted by the pair of slanted sides 1c'', and enters the pupil.

Thus, the examinee can see three images in total: a virtual image having the height P-Q seen through the top side 1c' and a pair of virtual images 3i' and 3i', each having the height p'-q' which is approximately the same height P-Q and seen above and below the image having the height P-Q.

Accordingly, when the illuminated LEDs 3 move successively at prescribed intervals, eye movement is observed and tested when the examinee follows the three moving images: one at the center and two above and below it, thereby giving the eyes a stimulus similar to the movement of striped-light movement. In this case, the images are separated into three as opposed to stripes as in the previous two cases, and each images looks slightly brighter.

Though the embodiment describes an eye movement photographing device equipped with one target device for testing one eye, it is possible to test the OKN of both of the eyes simultaneously by installing two target devices horizontally.

When a pair of photographing devices each containing the target device as described above are installed side by side in a pair of goggles, movement of both eyes are simultaneously tested. Thus, the OKN difference between both eyes (to be used checking cerebral diseases) can be effectively checked.

In such an embodiment, the target, which is striped light, is arranged to move (or to look as if it is moving) horizontally, i.e., in the direction of the two eyes. However, it is possible to change the direction 90 degrees so that striped light target moves up and down. Further, the LEDs (visible light source) can be arranged on a flat plane, not on a circular arc centered around the rotational center of the eye movement, thus simplifying the structure of the device.

The above described embodiment for testing a single eye uses LEDs as a visible light source to make the target compact. However, it is possible to use a small lamp as the visible light source to make it slightly larger than the LED light source, enabling the both eyes to follow the movement of the striped light targets simultaneously. Thus, the electrical potential of the eyes can be measured through electrodes attached near the eyes using testing devices such as an ENG and/or an EOG for OKN tests.

As is evident from the above description, according the present invention:

The light emitted from the multiple visible light sources composing a light source group is controlled by a light controlling device so that light emission is repeated successively at prescribed intervals. Thus, the examinee can see, through the optical component which serves as a refractor, the movement of striped virtual images of visible light enlarged only in a direction perpendicular to the direction of movement of the images. As a result, the device of the present invention induces OKN without requiring conventionally used large-scale equipment in which the examinee sits in the center of a rotating drum having black and white patterns inside, nor is a large space required. Thus, a compact and convenient target device for eye movement testing is obtained by installing the target device in a pair of goggles, etc.

Even when the position of the eye slightly deviates, image viewing is not interrupted or disturbed, and changes in the target image are minimized.

Furthermore, the refractor (optical component) is very simple in structure and when a convex or trapezoid refractor is used, the images are brighter than in the case the lenticular plate.

We claim:

1. A target device for eye movement tests comprising multiple visible light sources provided on a prescribed plane which includes an ocular axis of an eye wherein the axis center of each of said visible light sources is positioned proximate to one another so as to be able to emit light in the direction of said eye, a group of light sources is provided so that the lighting thereof is controlled via a light-controlling means to keep the illuminated part moving successively at prescribed intervals on said plane, and an optical component with a prescribed width is provided in front of said eye so as to cover the entire length of said light source group so that the distance between both ends of a formed image is enlarged only in the direction intersecting said plane of the light source image viewed from said eye to be examined.

2. A target device according to claim 1, wherein the cross section of said optical component perpendicular to the lengthwise direction of said light source group is lenticular.

3. A target device according to claim 1, wherein the cross section of said optical component perpendicular to the lengthwise direction of said light source group is convex.

4. A target device according to claim 1, wherein the cross section of said optical component perpendicular to the lengthwise direction of said light source group is an equilateral trapezoid with the front top plane thereof crossing perpendicular to said plane.

5. A target device used in eye movement tests comprising a combination of a light group and a light refracting means which is provided between said light group and eye to be examined, wherein:

said light group is provided on a plane including the optical axis of an eye and consists of a plurality of light sources arranged so that light from each light source advances towards said eye and the axes of said lights are close to each other, said light sources being connected to a means for successively lighting said light sources at predetermined intervals; and said light refracting means enlarges images in a direction perpendicular to the axis of said light, said light refracting means being made of a material which passes light therethrough and has a convex surface which faces said eye.

6. A target device used in an eye movement testing device which comprises a casing having a concave front wall facing an eye to be examined and provided with an oblong opening, and a television camera installed in said casing, said target device comprising a light group and a light refractor, wherein:

said light group, provided on an inner surface of said front wall to cover said opening, consists of a plurality of light sources arranged side by side so that light from each light source advances towards said eye and the axes of said lights are close to each other, said light sources being connected to a means for successively lighting said light sources at predetermined intervals; and said light refractor, provided on an outer surface of said front wall to cover said opening with a space between said optical component and said light group, enlarges images in a direction perpendicular to said lights from said light sources.

* * * * *